United States Patent
Igarashi

(10) Patent No.: US 10,571,680 B2
(45) Date of Patent: Feb. 25, 2020

(54) IMAGE PICKUP APPARATUS AND ENDOSCOPE

(71) Applicant: OLYMPUS CORPORATION, Tokyo (JP)

(72) Inventor: Takatoshi Igarashi, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 287 days.

(21) Appl. No.: 15/654,133

(22) Filed: Jul. 19, 2017

(65) Prior Publication Data

US 2017/0322411 A1 Nov. 9, 2017

Related U.S. Application Data

(63) Continuation of application No. PCT/JP2015/051880, filed on Jan. 23, 2015.

(51) Int. Cl.
*A61B 1/06* (2006.01)
*G02B 23/24* (2006.01)
(Continued)

(52) U.S. Cl.
CPC ............ *G02B 23/2484* (2013.01); *A61B 1/00* (2013.01); *A61B 1/00188* (2013.01);
(Continued)

(58) Field of Classification Search
CPC ............................. A61B 1/051; A61B 1/00163; G02B 23/2407; G02B 23/2423; G02B 23/243;
(Continued)

(56) References Cited

U.S. PATENT DOCUMENTS

2002/0176172 A1 11/2002 Nemoto et al.
2002/0186478 A1 12/2002 Watanabe et al.
(Continued)

FOREIGN PATENT DOCUMENTS

EP 2719319 A1 4/2014
JP S63-136781 A 6/1988
(Continued)

OTHER PUBLICATIONS

International Search Report dated Apr. 14, 2015 issued in PCT/JP2015/051880.
(Continued)

*Primary Examiner* — Matthew J Kasztejna
(74) *Attorney, Agent, or Firm* — Scully, Scott, Murphy & Presser, P.C.

(57) ABSTRACT

An image pickup apparatus includes an optical unit in which a plurality of lenses have relative positions fixed by a transparent resin that fills spaces among the plurality of lenses, and an image pickup substrate in which a light receiving section configured to receive light that is caused to be incident from the optical unit is formed on a principal surface, the optical unit being bonded to the principal surface via an adhesive, and the optical system includes an objective optical system including a plurality of lenses, and inter-lens distances of the plurality of lenses are defined by a spacer, a diaphragm, or the transparent resin.

11 Claims, 6 Drawing Sheets

(51) Int. Cl.
*A61B 1/00* (2006.01)
*A61B 1/05* (2006.01)
*A61B 1/005* (2006.01)
*H04N 5/374* (2011.01)

(52) U.S. Cl.
CPC ............ *A61B 1/051* (2013.01); *A61B 1/0051* (2013.01); *H04N 5/374* (2013.01)

(58) Field of Classification Search
CPC ............ G02B 23/2484; H04N 5/2251; H04N 5/2252; H04N 5/2257; H04N 5/2254
USPC .......................................... 600/129, 176–177
See application file for complete search history.

(56) References Cited

U.S. PATENT DOCUMENTS

| | | |
|---|---|---|
| 2002/0186936 A1 | 12/2002 | Freyhold et al. |
| 2004/0047274 A1 | 3/2004 | Amanai |
| 2009/0050946 A1 | 2/2009 | Duparre et al. |
| 2010/0085466 A1 | 4/2010 | Fujimori et al. |
| 2014/0078280 A1 | 3/2014 | Yoshida |
| 2016/0178884 A1* | 6/2016 | Hanada ................ G02B 23/243 359/738 |

FOREIGN PATENT DOCUMENTS

| | | |
|---|---|---|
| JP | H11-023980 A | 1/1999 |
| JP | 2000-271066 A | 10/2000 |
| JP | 2000-329985 A | 11/2000 |
| JP | 2002-045333 A | 2/2002 |
| JP | 2002-095626 A | 4/2002 |
| JP | 2002-112957 A | 4/2002 |
| JP | 2002-365560 A | 12/2002 |
| JP | 2003-180621 A | 7/2003 |
| JP | 2003-209751 A | 7/2003 |
| JP | 2003-337206 A | 11/2003 |
| JP | 2004-088713 A | 3/2004 |
| JP | 2005-052315 A | 3/2005 |
| JP | 2007-041398 A | 2/2007 |
| JP | 2008-508545 A | 3/2008 |
| JP | 2009-033132 A | 2/2009 |
| JP | 2010-078749 A | 4/2010 |
| JP | 2010-119039 A | 5/2010 |
| JP | 2012-254176 A | 12/2012 |
| JP | 2014-036799 A | 2/2014 |
| WO | WO 2012/169444 A1 | 12/2012 |

OTHER PUBLICATIONS

Extended Supplementary European Search Report dated Sep. 28, 2018 in European Patent Application No. 15 87 8812.5.

* cited by examiner

IMAGE PICKUP APPARATUS AND ENDOSCOPE

CROSS REFERENCE TO RELATED APPLICATION

This application is a continuation application of PCT/JP2015/051880 filed on Jan. 23, 2015, the entire contents of which are incorporated herein by this reference.

BACKGROUND OF THE INVENTION

1. Field of the Invention

The present invention relates to an image pickup apparatus including an optical system having a plurality of optical members, and an image pickup substrate in which a light receiving section is formed on a principal surface and the optical system is placed on the principal surface, and an endoscope including the image pickup apparatus.

2. Description of the Related Art

Electronic endoscopes have been widely used, which include image pickup apparatuses having solid image pickup devices such as CCDs, in distal end portions of insertion portions. A medical endoscope performs observation and the like of a site to be examined by an elongated insertion portion having flexibility with an image pickup apparatus contained in a distal end portion being inserted into a body cavity of a subject such as a patient.

In an image pickup apparatus for use in an endoscope or the like, outer circumferential portions of a plurality of lenses configuring an objective optical system are held by frame members of a metal, and an optical axis and inter-lens distances are defined. Reduction in diameter of the insertion portion has been required of an endoscope for the purpose of reducing invasiveness.

Japanese Patent Application Laid-Open Publication No. 2000-271066 and Japanese Patent Application Laid-Open Publication No. 2002-45333 each discloses an image pickup apparatus in which in order to reduce a diameter of an insertion portion, a space is provided in an optical path direction in a frame member, and an outer circumferential surface of the space portion is cut, and thereafter, the cut portion is disposed in close vicinity to a top surface side of a solid image pickup device, whereby a height dimension is reduced.

Note that Japanese Patent Application Laid-Open Publication No. 2007-41398 discloses a configuration in which a plurality of lenses are inserted into a frame member and fixed in a state in which an elastic substance is filled in spaces among the plurality lenses to hold the plurality of lenses temporarily.

SUMMARY OF THE INVENTION

An image pickup apparatus of an embodiment of the present invention includes an optical system in which a plurality of optical members have relative positions fixed by a transparent resin that fills spaces among the plurality of optical members, and an image pickup substrate in which a light receiving section configured to receive light that is caused to be incident from the optical system is formed on a principal surface, the optical system being bonded to the principal surface via an adhesive, wherein the optical system includes an objective optical system including a plurality of lenses, and inter-lens distances of the plurality of lenses are defined by a spacer, a diaphragm, or the transparent resin.

Further, an endoscope of another embodiment includes, in a distal end portion of an insertion portion, an image pickup apparatus including an optical system in which a plurality of optical members have relative positions fixed by a transparent resin that fills spaces among the plurality of optical members, and an image pickup substrate in which a light receiving section configured to receive light that is caused to be incident from the optical system is formed on a principal surface, the optical system being bonded to the principal surface via an adhesive, wherein the optical system includes an objective optical system including a plurality of lenses, and inter-lens distances of the plurality of lenses are defined by a spacer, a diaphragm, or the transparent resin.

DETAILED DESCRIPTION OF THE PREFERRED EMBODIMENT(S)

First Embodiment

At first, with use of FIG. 1, an endoscope 2 having an image pickup apparatus 10 of a first embodiment of the present invention, and an endoscope system 1 including the endoscope 2 will be described.

Note that the drawings are schematic, and attention should be paid to that relationships among thicknesses and widths of respective portions, ratios of the thicknesses of the respective portions and the like differ from the relationships, the ratios and the like in reality, and parts in which the relationships and the ratios of mutual dimensions differ may be included among the drawings.

Figure 1:
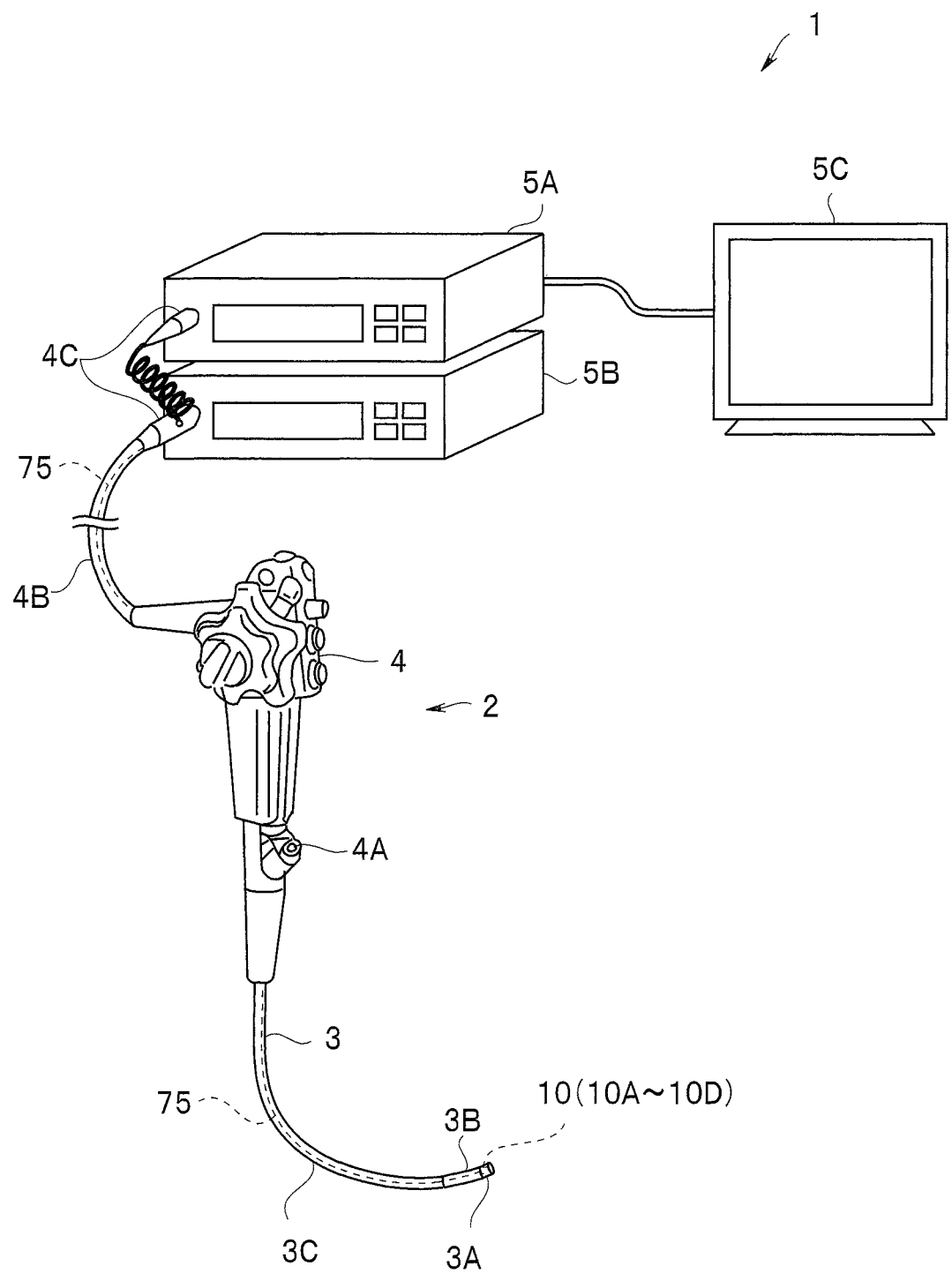
FIG. 1 is an outside view of an endoscope system including an endoscope of an embodiment.

As illustrated in FIG. 1, the endoscope system 1 includes the endoscope 2, a processor 5A, a light source apparatus 5B, and a monitor 5C. The endoscope 2 picks up an in-vivo image of a subject and outputs an image pickup signal by an insertion portion 3 being inserted into a body cavity of the subject.

At a proximal end side of the insertion portion 3 of the endoscope 2, an operation portion 4 provided with various buttons configured to operate the endoscope 2 is placed. The operation portion 4 has a treatment instrument insertion port 4A of a channel 3H configured to insert treatment instruments such as biological forceps, an electric knife and an inspection probe into a body cavity of a subject.

The insertion portion 3 is configured by a distal end portion 3A in which the image pickup apparatus 10 is placed, a bendable bending portion 3B connectively provided at a proximal end side of the distal end portion 3A, and a flexible tube portion 3C connectively provided at a proximal end side of the bending portion 3B. The bending portion 3B bends by an operation of the operation portion 4.

A signal cable 75 that is connected to the image pickup apparatus 10 of the distal end portion 3A is inserted through a universal cord 4B that is placed at a proximal end portion side of the operation portion 4.

The universal cord 4B is connected to the processor 5A and the light source apparatus 5B via a connector 4C. The processor 5A controls the entire endoscope system 1, and performs signal processing to an image pickup signal that is outputted by the image pickup apparatus 10 to output the image pickup signal as an image signal. The monitor 5C displays the image signal that is outputted by the processor 5A.

The light source apparatus 9 has a white LED, for example. White light that is emitted by the light source apparatus 9 is guided to an illumination optical systems 3D (refer to FIG. 2B) at the distal end portion 3A via a light guide (not illustrated) that is inserted through the universal cord 4B, and illuminates an object.

Figure 2A:
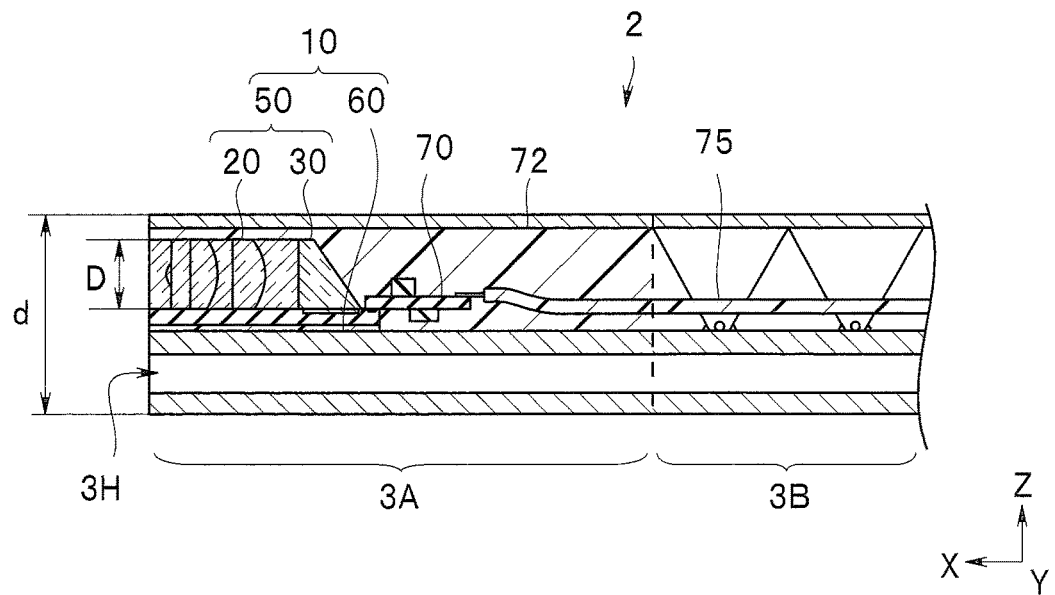
FIG. 2A is a sectional view of an insertion portion distal end portion of the endoscope of the embodiment.
Figure 2B:
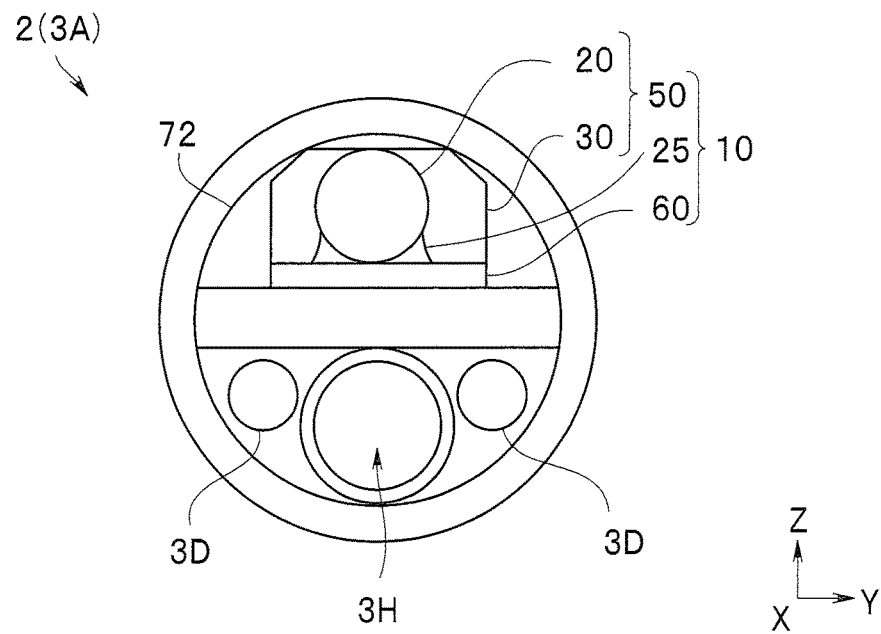
FIG. 2B is a transparent schematic diagram of the insertion portion of the endoscope of the embodiment at a time of the insertion portion being observed from a distal end portion direction of the insertion portion.

Next, a configuration of the distal end portion 3A of the endoscope 2 will be described with use of FIG. 2A and FIG. 2B.

In the distal end portion 3A, the image pickup apparatus 10 and the treatment instrument channel 3H are placed. The illumination optical systems 3D that emit illuminating light are also placed in the distal end portion 3A.

The image pickup apparatus 10 includes an optical unit 50 that is an optical system including an objective optical system (hereinafter, also referred to as a "lens unit") 20 and a prism 30, and an image pickup substrate 60. The image pickup apparatus 10 has a rear end portion sealed by a sealing resin 72.

The image pickup substrate 60 where the optical unit 50 is surface-mounted is connected to the signal cable 75 via a wiring board 70. Note that a proximal end outer circumferential portion of the distal end portion 3A is covered with a flexible covering tube not illustrated.

In a conventional endoscope configured such that outer circumferential portions of a plurality of lenses constituting an objective optical system are held by a metal frame member, to define the optical axis and inter-lens distances, it is not easy to reduce a wall thickness of the metal frame member to a predetermined value or less due to a limitation of metal work. Consequently, in the objective optical system of small-diameter lenses, the wall thickness of the frame member becomes relatively larger as compared with the outside diameters of the lenses, and reduction in diameter has been limited. In the case of using a resin as the material of the frame member, reduction in diameter is limited because the wall thickness is restricted due to a limitation of the injection molding technique, for example.

In particular, in a bronchoscope and a nasal insertion type endoscope, the outside diameters of the insertion portions are extremely thin, and several millimeters. Therefore, further reduction in diameter has not been easy in the conventional endoscope configured such that outer circumferential portions of the plurality of lenses constituting the objective optical system are held by the metal frame member, to define the optical axis and inter-lens distances.

The endoscope 2 is, for example, a nasal insertion type endoscope in which a diameter d of the distal end portion 3A including a thickness of the covering tube is 3 mm or less. The objective optical system 20 (refer to FIG. 4) of the image pickup apparatus 10 has an extremely small diameter with a diameter D of 1 mm or less, and an outer dimension in a perpendicular direction to an optical axis of the image pickup apparatus 10 is microminiaturized and 1.5 times as large as the diameter D, for example. Note that the endoscope of the embodiment may be an endoscope specially meant for observation with a smaller diameter in which the treatment instrument channel 311 is not placed.

<Configuration of Image Pickup Apparatus>

Next, a configuration of the image pickup apparatus 10 of the present embodiment will be described in detail.

Figure 3:
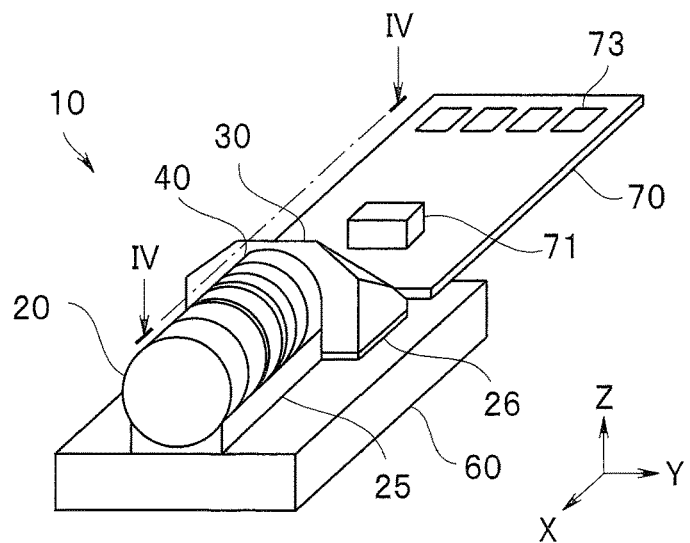
FIG. 3 is a perspective view of an image pickup apparatus of a first embodiment.
Figure 4:
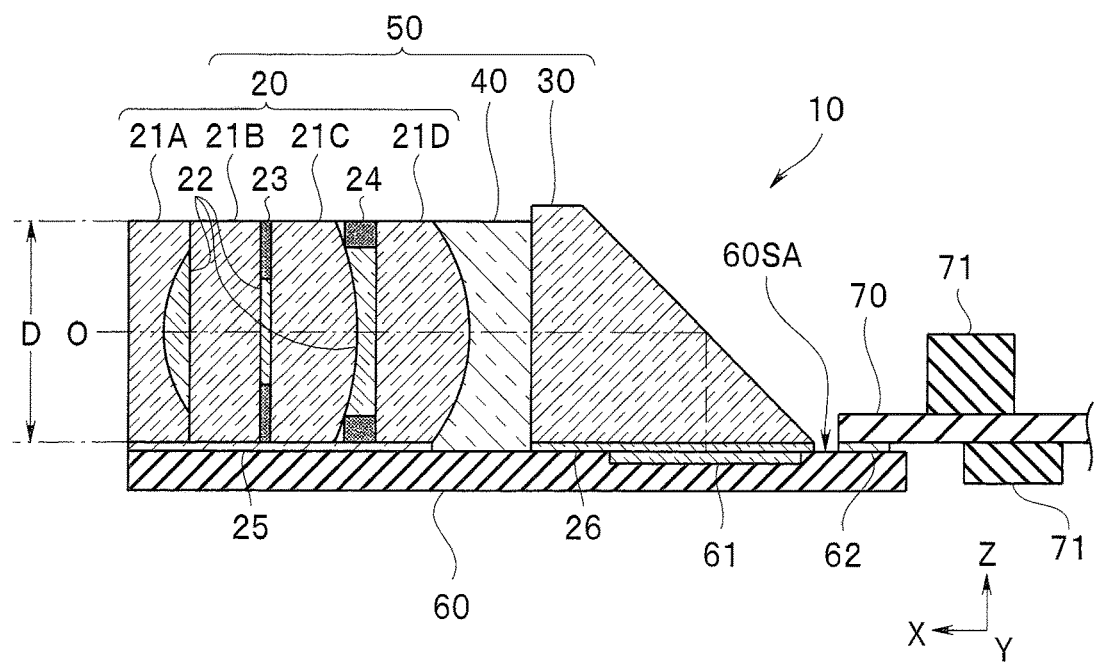
FIG. 4 is a sectional view taken along line IV-IV in FIG. 3, of the image pickup apparatus of the first embodiment.

As illustrated in FIG. 3 and FIG. 4, the image pickup apparatus 10 is of a so-called "horizontally-placed type" in which an optical axis O of the objective optical system 20 is parallel with a principal surface 60SA of the image pickup substrate 60.

In the optical unit 50, relative positions of a plurality of lenses 21A to 21D and the prism 30 which are optical members are fixed by transparent resins 22 and 40 that fill spaces among the optical members. Note that hereinafter, each of the plurality of lenses 21A to 21D is referred to as a lens 21. A number of lenses 21 are two to ten inclusive.

The image pickup substrate 60 where a light receiving section 61 is formed on the principal surface 60SA is formed from a semiconductor such as silicon. The light receiving section 61 is a CMOS (complementary metal oxide semiconductor) type semiconductor circuit, or a CCD (charge coupled device). In an end portion of the image pickup substrate 60, a plurality of electrode pads 62 that are electrically connected to the light receiving section 61 are placed. The wiring board 70 on which electronic components 71 are mounted is bonded to the electrode pads 62. A plurality of connection electrodes 73 of the wiring board 70 are bonded to the signal cable 75.

The lens unit 20 of the image pickup apparatus 10 is directly bonded to the principal surface 60SA of the image pickup substrate 60 via an adhesive layer 25 formed from an ultraviolet curing type resin. That is, the image pickup apparatus 10 does not include a frame body (frame member) that is a member which supports an outer circumferential portion of the lens 21.

Further, the prism 30 is also bonded to the principal surface 60SA of the image pickup substrate 60 via an adhesive layer 26 formed from an ultraviolet curing type resin. The ultraviolet curing type transparent resin 40 is also filled in a space between the lens unit 20 and the prism 30.

Light that is incident on the optical unit 50 is condensed by the lens unit 20 and is incident on the prism 30. The prism 30 reflects the incident light from the lens unit 20 to emit the light to the light receiving section 61. The light receiving section 61 receives the light emitted by the prism 30, and converts the received light into an image pickup signal. The image pickup signal outputted by the image pickup apparatus 10 is transmitted to the processor 5A via the wiring board 70 and the signal cable 75.

Here, a large and heavy lens cannot be held stably unless the lens is fixed by a frame body. However, in the image pickup apparatus 10, the lens 21 is extremely small in diameter and extremely light, and therefore can be stably held by the transparent resin 22. Note that in order to hold the lens 21 stably, the diameter D of the lens 21 is preferably 1 mm or less, and is more preferably 0.5 mm or less. Due to a limitation of working precision, a lower limit of the diameter D is preferably 0.1 mm or more, for example.

A refractive index n1 of the lens 21 is preferably 1.2 times or more as high as a refractive index n2 of the transparent resins 22 and 40. Note that the refractive index n1 is more preferably 1.5 times to two times as high as the refractive index n2 or is two times as high as the refractive index n2. When the refractive index n1 is within the aforementioned range, optical design is easy. Further, in view of easiness of material selection, the refractive index n2 is preferably 1.05 or more. For example, when the refractive index n1 is 2.0, the refractive index n2 is more preferably 1.05 or more. In accordance with the refractive index n1 and the refractive index n2, optical design of a lens curvature, inter-lens distances and the like is performed. Furthermore, light transmittances of the transparent resins 22 and 40 in a visible light band are preferably 90% or more.

Note that as illustrated in FIG. 4, the lens unit 20 of the image pickup apparatus 10 has a diaphragm 23 that defines a thickness of a luminous flux, and the inter-lens distance is defined by a spacer 24. The diaphragm 23 may define the inter-lens distance, or the lenses are directly bonded to one another.

The image pickup apparatus 10 having the lens unit 20 in which the plurality of lenses 21 are fixed by the transparent resin 22 in place of frame bodies is small in diameter. Further, since the transparent resin 22 is filled in the spaces among the plurality of lenses 21 in the image pickup apparatus 10, gas that is generated when the sealing resin 72 is subjected to curing treatment, foreign matters and the like do not enter the spaces among the plurality of lenses. Further, water tightness is ensured in the spaces among the plurality of lenses 21, and therefore, fogging does not occur due to entry of moisture and a temperature change. Furthermore, an exclusive shielding member for preventing entry of foreign matters or the like is not required, so that the diameter is small <Manufacturing Method of Image Pickup Apparatus>

Next, a manufacturing method of the image pickup apparatus 10 will be described briefly.

The image pickup substrate 60 is produced by using a known semiconductor technique. Further, the lenses 21, the prism 30, the diaphragm 23 and the spacer 24 are produced in accordance with specifications. The lenses 21 and the prism 30 are formed from glass or a transparent resin. The diaphragm 23 and the spacer 24 are formed from a metal or a resin.

At first, the diaphragm 23 or the spacer 24 is placed on the lens 21. For example, the lens 21 held by a jig is moved onto the spacer 24, and after positioning is performed, both the spacer 24 and the lens 21 are bonded to each other by an adhesive. The adhesive used here may be a same resin as the transparent resin 22, or a nontransparent resin, but is preferably an ultraviolet curing type resin.

Further, after a metal film of a predetermined film thickness is deposited on a surface of the lens 21, a metal film of an optical path portion is removed by etching or the like, and the lens 21 with which the diaphragm 23 or the spacer 24 is integrated may be produced.

Next, the lens unit 20 is produced. The lenses 21A to 21D bonding surfaces of which are coated with the uncured transparent resin 22 are fixed to a jig exclusive for integration, and are irradiated with ultraviolet rays while the lenses 21A to 21D are pressed in the optical axis direction. The inter-lens distance is accurately defined by the spacer 24.

Further, the spacer 24 or the like is not bonded to the lens 21 in advance, but the lens 21 and the spacer 24 or the like may be fixed to a jig to be integrated simultaneously. After the lens 21 or the like is fixed to the jig, the transparent resin 22 may be filled.

Further, in order to define the inter-lens distance, an amount of the transparent resin 22 that is filled in the spaces among the plurality of lenses 21 may be controlled, or a jig with high precision of the spaces among the lenses to be held may be used, instead of the spacer 24. In the very small lens unit 20, the inter-lens distances are very small, and the spacer 24 is thin correspondingly. Consequently, requirements for working size and working precision of the spacer 24 are stiff, and working is extremely difficult. The inter-lens distances are defined by the transparent resin 22 without use of the spacer 24, and thereby a problem of working of the spacer 24 can be solved.

Figure 5:
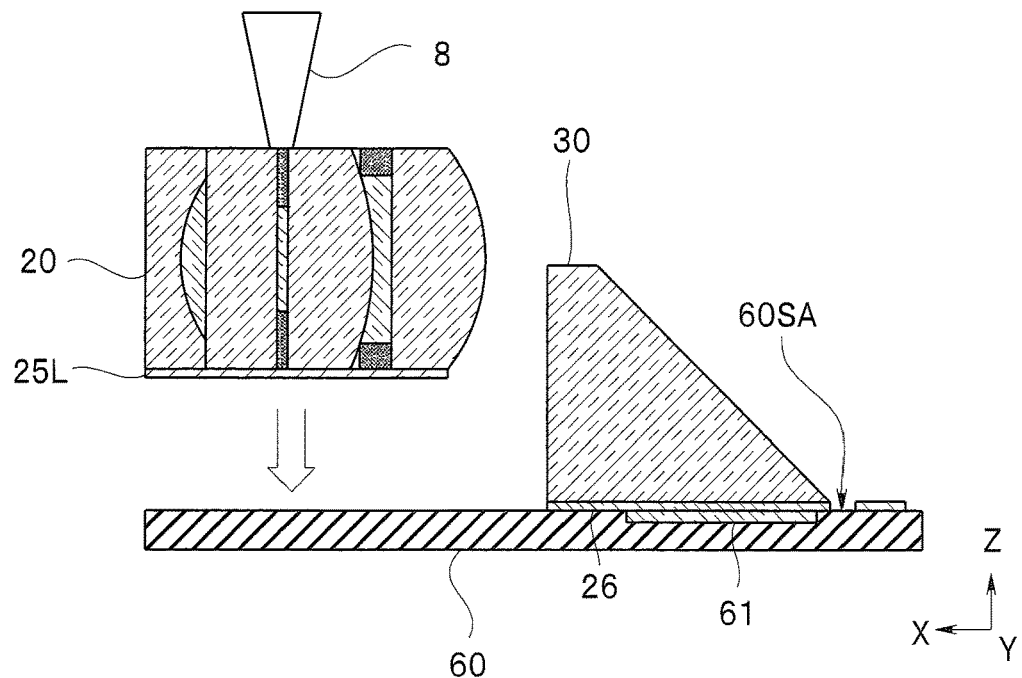
FIG. 5 is a sectional view for explaining a manufacturing method of the image pickup apparatus of the first embodiment.

Subsequently, as illustrated in FIG. 5, the lens unit 20 coated with an uncured adhesive 25L is held by a suction tool 8, is positioned to a predetermined position, and is irradiated with ultraviolet rays, whereby the lens unit 20 is bonded to the image pickup substrate 60 via an adhesive layer 25. The adhesive 25L may be coated after positioning. Further, the adhesive 25L may be coated on a predetermined position of the image pickup substrate 60, and the lens unit 20 may be mounted on the predetermined position.

Though not illustrated, the prism 30 held by a suction tool is positioned to the light receiving section 61 coated with an adhesive formed from an ultraviolet curing type transparent resin. Subsequently, the adhesive is cured when the adhesive is irradiated with ultraviolet rays, and therefore the prism 30 is bonded to the image pickup substrate 60 via an adhesive layer 26.

Figure 6:
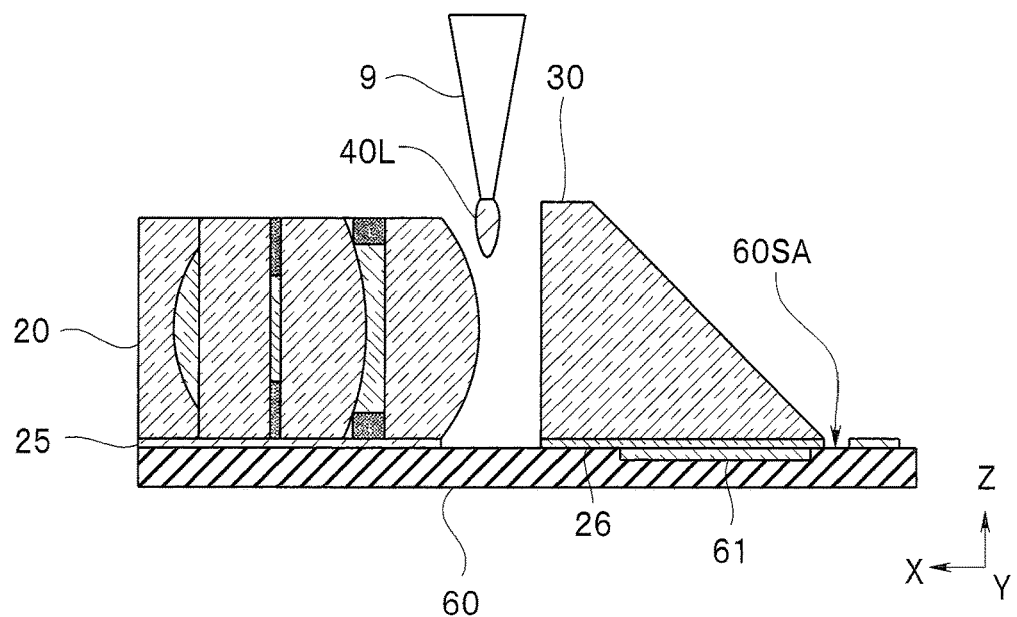
FIG. 6 is a sectional view for explaining the manufacturing method of the image pickup apparatus of the first embodiment.

Subsequently, as illustrated in FIG. 6, an uncured transparent resin 40L is filled in the space between the lens unit 20 and the prism 30 with use of a dispense nozzle or the like, and is irradiated with ultraviolet rays. Note that as will be described later, in a case where the wiring board 70 is bonded to the image pickup substrate 60 in advance, a bonding portion of the image pickup substrate 60 and the wiring board 70 may be sealed with the transparent resin 40 simultaneously with a time of the transparent resin 40 being filled. In this case, reliability of the image pickup apparatus 10 can be enhanced at low cost without a sealing step being additionally provided.

Note that the transparent resin 22, the transparent resin 40, the adhesive layer 26 and the adhesive layer 25 may be a same resin, or the adhesive layer 25 and the transparent resin 40 may be a same resin that is coated simultaneously. Note that in order to prevent displacement from the position where positioning is performed due to curing shrinkage, a resin/adhesive with a low curing shrinkage rate is preferably used. Further, in order to cure the resin immediately in a positioned state, an ultraviolet curing type of resin/adhesive is preferably used as already described.

Outer surfaces of the lens unit 20 and the prism are painted in a black ink or the like, whereby stray light can be prevented from entering the light receiving section 61. Note that vacuum degassing treatment is preferably performed for the transparent resin 40 or the like, which is to be the optical path, in an uncured state, and entry of gas bubbles is preferably prevented.

Here, the wiring board 70 may be bonded to the image pickup substrate 60 before the lens unit 20 is bonded to the image pickup substrate 60, or before the transparent resin 40L is filled, and an image pickup signal outputted by the light receiving section 61 may be displayed on the monitor 5C, or the image pickup signal may be confirmed by an evaluation device or the like.

For example, before the lens unit 20 is bonded to the image pickup substrate 60, so-called active alignment, is performed, which adjusts a position of the lens unit 20 while the image pickup signal is confirmed and actively aligns the lens unit 20, and thereby positioning can be performed with higher precision. When active alignment is performed, the transparent resin 40L is filled on an undersurface of the lens unit 20 and in the space between the lens unit 20 and the prism 30, in a state where the lens unit 20 is disposed in the predetermined position by using the suction tool 8, and thereafter the position is adjusted. Curing of the transparent resin 40L is performed by ultraviolet irradiation after position adjustment, whereby bonding of the lens unit 20 is also performed simultaneously.

Further, after the lens unit 20 is bonded to the image pickup substrate 60, before the transparent resin 40L is filled, evaluation of a resolution or the like of the image pickup apparatus 10 is performed, and in order to obtain a desired resolution in accordance with an evaluation result, the transparent resin 40L to be filled may be selected from a plurality resins having different refractive indexes. Thereby, even when variations are present in the position of the objective optical system and assembly of the objective optical system, it becomes possible to obtain a desired resolution.

<Modifications of First Embodiment>

Next, image pickup apparatuses 10A to 10C of modifications 1 to 3 of the first embodiment will be described. The image pickup apparatuses 10A to 10C of the modifications are similar to the image pickup apparatus 10 of the first embodiment in configuration, and have a same effect as the effect of the image pickup apparatus 10. Consequently, the components of same functions as in the image pickup apparatus 10 will be assigned with same reference signs and explanation of the components will be omitted.

<Modification 1>

Figure 7:
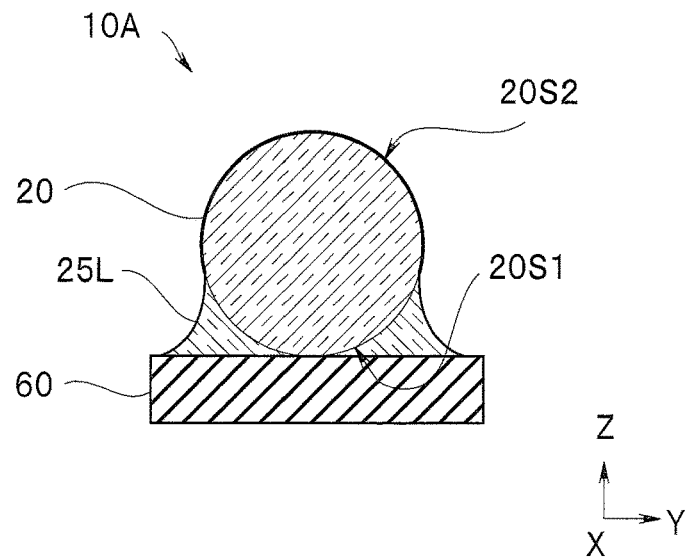
FIG. 7 is a sectional view for explaining an image pickup apparatus of modification 1 of the first embodiment 1.

In the image pickup apparatus 10A of modification 1, an ultraviolet curing type adhesive 25L before cured is hydrophilic. As illustrated in FIG. 7, in the lens unit 20, a region 20S1 that is bonded to the image pickup substrate 60, on an outer circumferential surface is hydrophilic, and a region 20S2 (that is not bonded) except for the region 20S1, on the outer circumferential surface is hydrophobic. The hydrophilic surface is formed by ultraviolet irradiation, plasma irradiation, coating with a hydrophilic polymer, blasting work or the like. The hydrophobic surface is formed by coating with a hydrophobic polymer or the like.

In the image pickup apparatus 10A, "crawling-up" of the adhesive 25L onto an outer circumferential portion of the lens unit 20 can be prevented, so that an outer shape does not become large, and reduction in diameter is easy.

<Modification 2>

Figure 8:
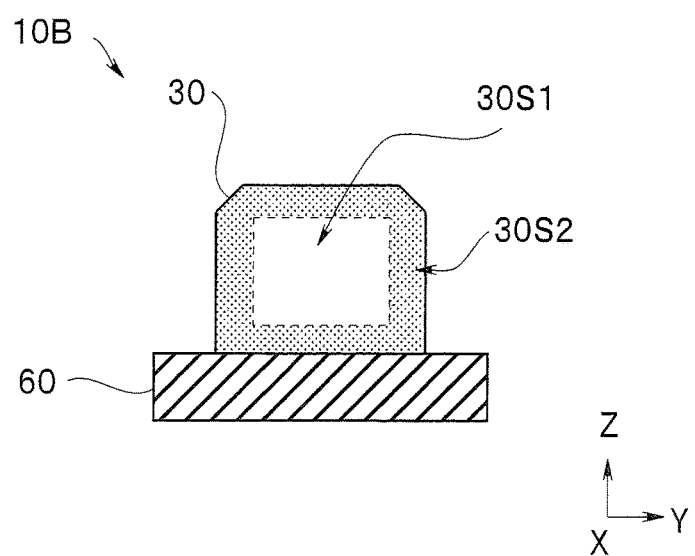
FIG. 8 is a sectional view for explaining an image pickup apparatus of modification 2 of the first embodiment.

In an image pickup apparatus 10B of modification 2, the transparent resin 40 which fills the space between the lens unit 20 and the prism 30 is hydrophilic before the transparent resin 40 is cured (40L). As illustrated in FIG. 8, in the prism 30, a region 30S2 around an optical effective region 30S1 on a surface that is in contact with the transparent resin 40 is hydrophilic.

The hydrophilic region 30S2 is formed by hydrophilization treatment such as ultraviolet irradiation, plasma irradiation, coating with a hydrophilic polymer, or blasting work. For example, the effective region 30S1 is masked, and hydrophilization treatment is applied to only the surrounding region 30S2. Since the effective region 30S1 is not treated, the hydrophilization treatment does not exert a bad influence on image pickup characteristics and the like.

In the image pickup apparatus 10B, the uncured transparent resin 40L easily wets and spreads on a region in an outer circumference of the prism 30. Consequently, an interface between the transparent resin 40 and air, which is generated as a result of the air remaining on the surface of the prism 30 due to insufficient spread of the transparent resin 40L, can be prevented from being taken into an image.

<Modification 3>

Figure 9:
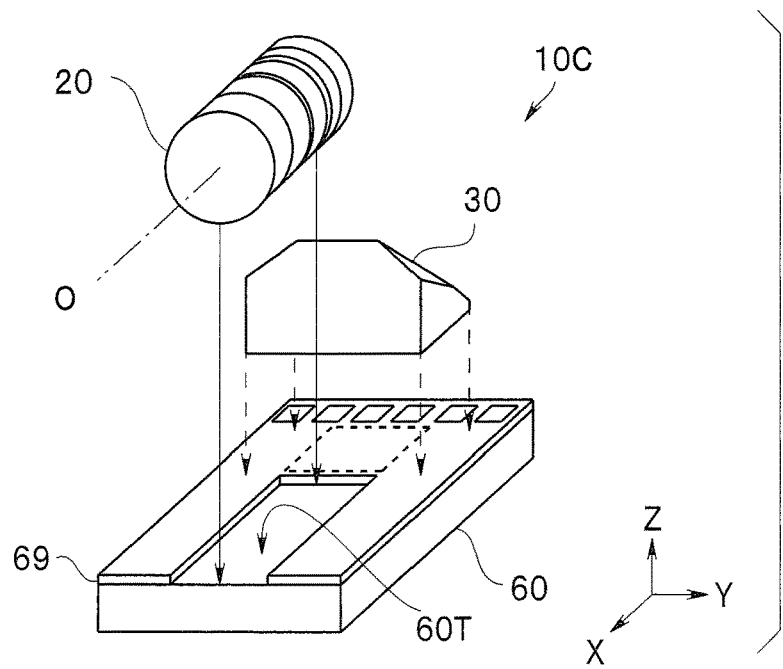
FIG. 9 is a perspective exploded view for explaining an image pickup apparatus of modification 3 of the first embodiment.

As illustrated in FIG. 9, in an image pickup apparatus 10C of modification 3, a concave portion 60T, which is laterally symmetrical with respect to the optical axis O, is formed in a region to which the lens unit 20 of the image pickup substrate 60 is bonded and fixed.

Not illustrated so far, a coat layer 69 formed of a color filter and a protection film is placed on the principal surface 60SA of the image pickup substrate 60. In the image pickup apparatus 10C, the coat layer 69 is patterned, whereby the concave portion 60T which is laterally symmetrical with respect to the optical axis O is formed.

In the image pickup apparatus 10C, the uncured adhesive 25L stays in the concave portion 60T, and the adhesive 25L is disposed laterally symmetrically with respect to the optical axis O. Consequently, tensile stress by curing shrinkage of the adhesive 25L is applied to the lens unit 20 laterally symmetrically, and therefore misalignment can be prevented. Note that wiring and the like are not formed in a region that forms the concave portion 60T, and therefore, even when the coat layer 69 is removed, a bad influence is not exerted on the characteristics and reliability.

Second Embodiment

Next, an image pickup apparatus 10D of a second embodiment will be described. The image pickup apparatus 10D is analogous to the image pickup apparatus 10 of the first embodiment, so that components having same functions are assigned with same reference signs, and explanation will be omitted.

Figure 10:
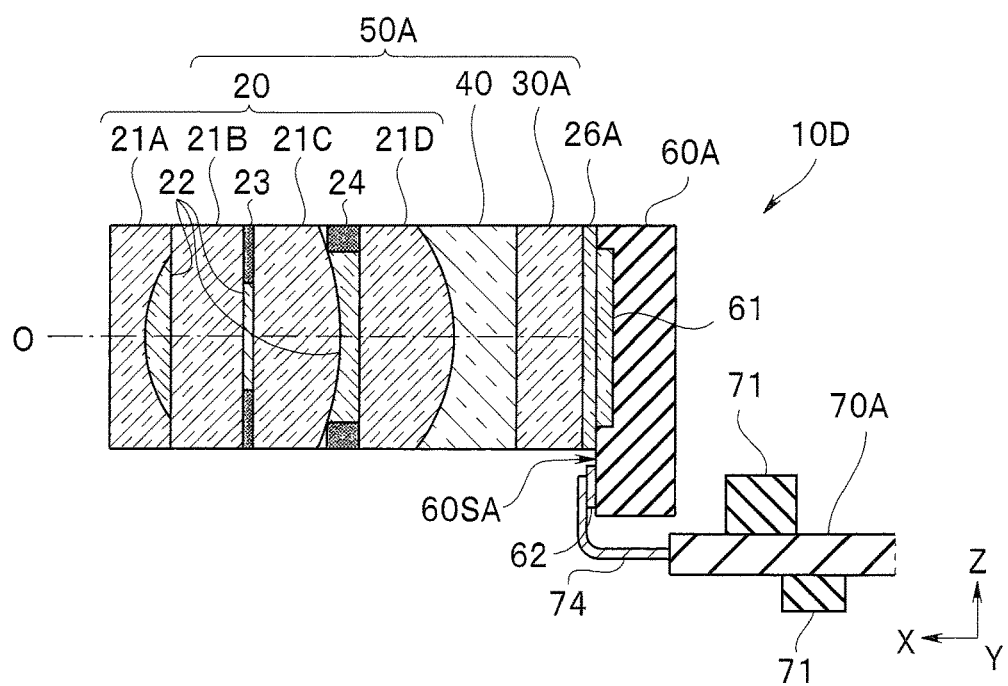
FIG. 10 is a sectional view of an image pickup apparatus of a second embodiment.

As illustrated in FIG. 10, in the image pickup apparatus 10D, an optical unit 50A that is an optical system has a cover glass (glass lid) 30A that is bonded with an adhesive 26A in such a manner as to cover the light receiving section 61 of an image pickup substrate 60A. The image pickup apparatus 10D is of a so-called "vertically-placed type" in which the optical axis O of the lens unit 20 that is an objective optical system is perpendicular to the principal surface 60SA of the image pickup substrate 60. A wiring board 70A is bonded to the electrode pad 62 via a flying lead 74.

In a manufacturing process, the transparent resin 40L is coated on the cover glass 30A in a state in which the principal surface 60SA of the image pickup substrate 60 is disposed horizontally.

Subsequently, after positioning of a horizontal direction (a YZ direction) and a vertical direction (an X direction) of the lens unit 20 is performed, ultraviolet irradiation is performed, and the lens unit 20 is fixed to the cover glass 30A.

In the image pickup apparatus 10D, a plurality of lenses 21A to 21D and the prism 30 have relative positions fixed by the transparent resins 22 and 40 that fill the spaces among the plurality of lenses 21A to 21D and the prism 30. Consequently, the image pickup apparatus 10D has a same effect as the effect of the image pickup apparatus 10.

As in the above explanation, the image pickup apparatus of the present invention includes an optical system (the optical unit 50) formed by a plurality of optical members (the lenses 21, the prism 30, the cover glass 30A) being separated from and bonded to one another by transparent resins (22, 40), and an image pickup device (the image pickup substrate 60) having the light receiving section 61 configured to generate an electric signal by receiving light incident from the optical system and performing photoelectric conversion, and the optical system is composed of an objective optical system (the lens unit 20) configured to condense incident light of an image pickup target, and optical elements (the prism 30, the cover glass 30A) configured to emit the incident light from the objective optical system to the light receiving section.

The present invention is not limited to the aforementioned embodiments and the like, and various modifications, alterations and the like can be made within the range without departing from the gist of the present invention. For example, the configurations described in modifications 1 to 3 of the first embodiment may be used in the image pickup apparatus 10D of the second embodiment. Further, as illustrated in FIG. 1, the endoscope 2 may include the image pickup apparatuses 1A to 1D, in the distal end portion 3A of the insertion portion 3.

What is claimed is:

1. An image pickup apparatus, comprising:
   an objective optical system comprising a plurality of lenses, positions of the plurality of lenses being fixed relative to each other by a transparent adhesive adhering each lens of the plurality of lenses to one or more adjacent lenses of the plurality of lenses, the transparent adhesive filling spaces between each lens and the one or more adjacent lenses to adhere each of the plurality of lenses to the one or more adjacent lenses; and
   an image pickup substrate having an image sensor, the image sensor having a light receiving section configured to receive incident light from the optical system, the light receiving section being formed on a principal surface of the image pickup substrate, an outer circumferential surface of the plurality of lenses being directly adhered to the principal surface via an adhesive,
   wherein inter-lens distances of the plurality of lenses are defined by a spacer, a diaphragm, or the transparent adhesive.

2. The image pickup apparatus according to claim 1, wherein diameters of the plurality of lenses are 1 mm or less.

3. The image pickup apparatus according to claim 2, wherein refractive indexes of the lenses are no less than 1.2 times as high as a refractive index of the transparent adhesive, the transparent adhesive being an ultraviolet curing type.

4. The image pickup apparatus according to claim 3, wherein relative positions of the plurality of lenses are fixed by the transparent adhesive.

5. The image pickup apparatus according to claim 4, wherein spaces among the plurality of lenses are defined by the spacer.

6. The image pickup apparatus according to claim 2, further comprising:
   a prism configured to reflect incident light from the objective optical system to emit the incident light to the light receiving section, and
   an optical axis of the objective optical system is parallel with the principal surface of the image pickup substrate.

7. The image pickup apparatus according to claim 6,
   wherein the adhesive before curing is hydrophilic, and
   in the objective optical system, a region of the outer circumferential surface that is adhered to the image pickup substrate is hydrophilic, and a region of the outer circumferential surface that is not adhered to the image pickup substrate is hydrophobic.

8. The image pickup apparatus according to claim 6,
   wherein the transparent resin fills a space between the objective optical system and the prism, the transparent resin being an ultraviolet curing type, and the transparent resin being hydrophilic before curing, and
   in the prism, surroundings of an optical effective region of a surface of the prism that is in contact with the transparent resin are hydrophilic.

9. The image pickup apparatus according to claim 6, wherein the image pickup substrate comprises a concave portion, the concave portion being formed in a region of the image pickup substrate laterally symmetrical with respect to the optical axis of the objective optical system, the outer circumferential surface of the lenses of the objective optical system being adhered to the concave portion.

10. The image pickup apparatus according to claim 2,
    wherein the objective optical system includes a cover glass adhered to the image pickup substrate so as to cover the light receiving section, and
    the optical axis of the objective optical system is perpendicular to the principal surface of the image pickup substrate.

11. An endoscope, comprising:
    an insertion portion having a distal end portion; and
    the image pickup apparatus according to claim 1 disposed in the distal end portion of the insertion portion.

* * * * *